(12) United States Patent
Green

(10) Patent No.: US 7,600,663 B2
(45) Date of Patent: Oct. 13, 2009

(54) APPARATUS FOR STAPLING AND INCISING TISSUE

(76) Inventor: David T. Green, 40 Madison Hill, Fairfield, CT (US) 06430

( * ) Notice: Subject to any disclaimer, the term of this patent is extended or adjusted under 35 U.S.C. 154(b) by 89 days.

(21) Appl. No.: 11/825,175

(22) Filed: Jul. 5, 2007

(65) Prior Publication Data

US 2009/0008424 A1   Jan. 8, 2009

(51) Int. Cl.
*A61B 17/068* (2006.01)
(52) U.S. Cl. ............ 227/175.2; 227/180.1; 227/19
(58) Field of Classification Search ........... 227/180.1, 227/175.2, 19
See application file for complete search history.

(56) References Cited

U.S. PATENT DOCUMENTS

| 3,499,591 | A | | 3/1970 | Green | |
|---|---|---|---|---|---|
| 3,692,224 | A | * | 9/1972 | Astafiev et al. | 227/19 |
| 4,442,964 | A | * | 4/1984 | Becht | 227/8 |
| 4,522,327 | A | * | 6/1985 | Korthoff et al. | 227/19 |
| 4,527,724 | A | * | 7/1985 | Chow et al. | 227/8 |
| 4,591,085 | A | * | 5/1986 | Di Giovanni | 227/8 |
| 4,728,020 | A | * | 3/1988 | Green et al. | 227/19 |
| 5,240,163 | A | * | 8/1993 | Stein et al. | 227/175.3 |
| 5,307,976 | A | * | 5/1994 | Olson et al. | 227/175.3 |
| 5,312,023 | A | * | 5/1994 | Green et al. | 227/175.1 |
| 5,318,221 | A | * | 6/1994 | Green et al. | 227/178.1 |
| 5,326,013 | A | * | 7/1994 | Green et al. | 227/176.1 |
| 5,456,401 | A | * | 10/1995 | Green et al. | 227/176.1 |
| 5,478,003 | A | * | 12/1995 | Green et al. | 227/176.1 |
| 5,485,952 | A | | 1/1996 | Fontayne | |
| 5,560,532 | A | | 10/1996 | DeFonzo et al. | |
| 5,636,780 | A | * | 6/1997 | Green et al. | 227/176.1 |
| 5,645,209 | A | * | 7/1997 | Green et al. | 227/175.2 |
| 5,690,269 | A | | 11/1997 | Bolanos et al. | |
| 5,901,895 | A | | 5/1999 | Heaton et al. | |
| 5,993,464 | A | | 11/1999 | Knodel | |
| 6,250,532 | B1 | * | 6/2001 | Green et al. | 227/175.1 |
| 6,460,749 | B1 | | 10/2002 | Levinson et al. | |
| 6,619,529 | B2 | * | 9/2003 | Green et al. | 227/176.1 |

* cited by examiner

*Primary Examiner*—Brian D Nash
(74) *Attorney, Agent, or Firm*—Scott D. Wofsy; George N. Chaclas; Edwards Angell Palmer & Dodge LLP

(57) ABSTRACT

A surgical fastening and cutting assembly having a housing defines a passage and a pusher, with a cam surface, slides in the passage. An arm couples to the housing and an anvil base is located on the arm. A body slides on the arm between the housing and the base. The body defines a bore and a staple passage having a staple therein. A cam follower extends from the cartridge body to the housing. In an open position, tissue can be placed between the anvil base and the body. In an intermediate position, the cam surface of the pusher can move the cam follower into a locked position and, thereby, the tissue can be clamped. In a fastened and cut position, the pusher can move such that the staple can be been driven and formed in the tissue and a knife, coupled to the pusher, can cut the tissue.

7 Claims, 12 Drawing Sheets

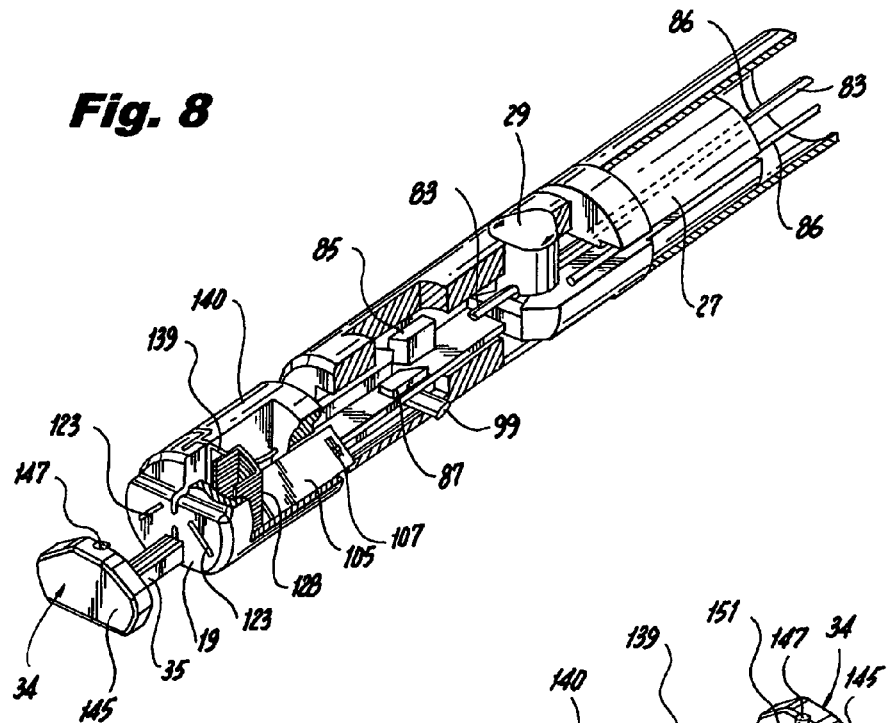

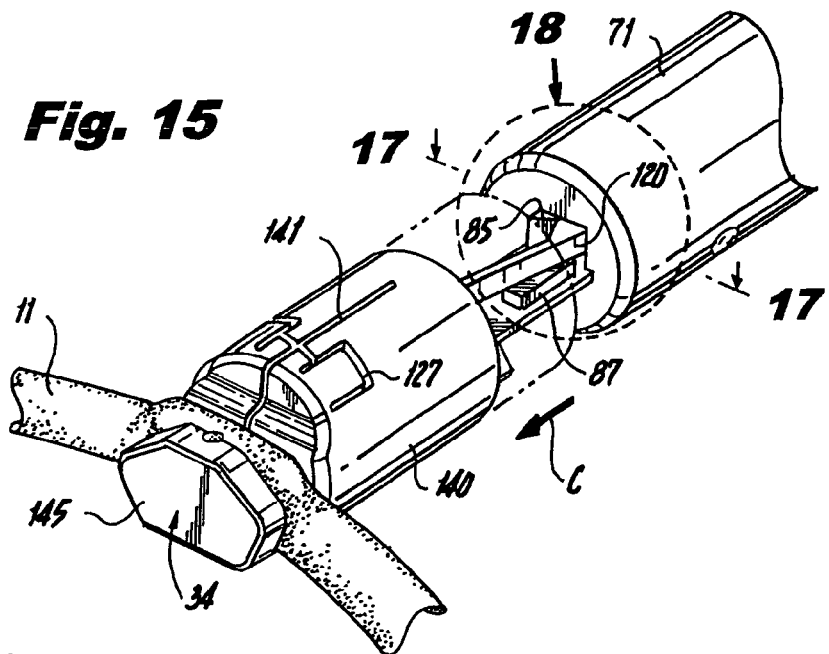
Fig. 15
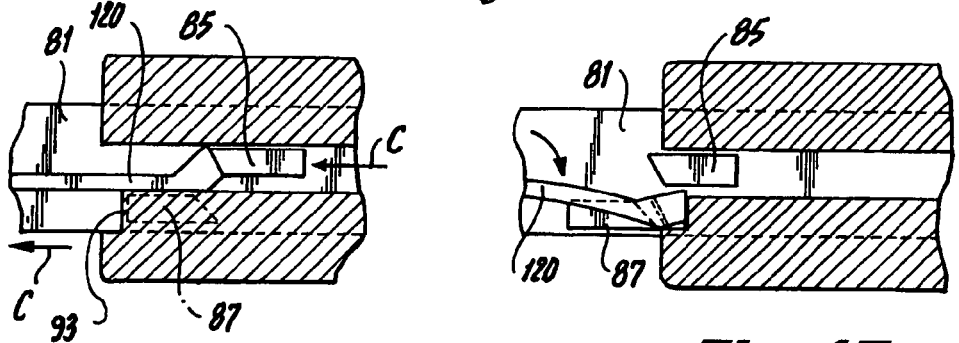
Fig. 16   Fig. 17
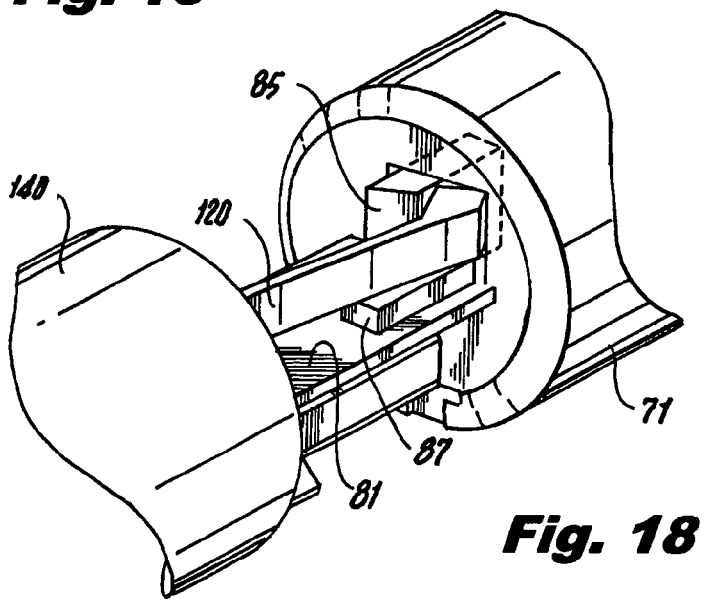
Fig. 18

APPARATUS FOR STAPLING AND INCISING TISSUE

BACKGROUND OF THE INVENTION

1. Field of the Invention

The subject disclosure relates to surgical instruments and methods for cutting and applying surgical staples to body tissue, and more particularly, to a surgical instrument for forming an incision in body tissue while placing staples on each side of the incision.

2. Background of the Related Art

Many surgical procedures often require the application of one or more surgical fasteners to body organs and tissue. In many instances, the fasteners used are unitary metal staples. Such metal staples are used in numerous types of surgical procedures. In most surgical procedures, the staples are applied directly to the body tissue requiring attachment, reattachment, ligation, etc. In certain other procedures, staples are used to attach an intermediate object to the body tissue. In still other procedures, cutting of the body tissue in areas adjacent the stapling is also desired.

In view of the above, surgical stapling instruments are known wherein tissue is first grasped or clamped between an opposing jaw structure and then fastened by means of fasteners. In some instruments, a knife is provided to cut tissue which has been joined by the fasteners. Instruments for this purpose can include two elongated jaws which are respectively used to capture or clamp tissue. Typically, one of the jaws carries a disposable cartridge wherein a plurality of staples are arranged in a row while the other jaw has an anvil for forming the staple legs as the staples are driven from the cartridge. Generally, the stapling operation is effected by a camming element which travels longitudinally through the cartridge and acts upon individual staple pushers to sequentially eject the staples from the cartridge. A knife can be positioned in such a manner so as to operate sequentially immediately behind the camming element and laterally positioned between the staple rows to longitudinally cut and/or open the stapled tissue. Such instruments are disclosed, for example, U.S. Pat. No. 3,490,675 to Green, U.S. Pat. No. 5,901,895 to Green and U.S. patent application Ser. No. 11/410,346 to Green, each of which is incorporated herein by reference.

An instrument disclosed in U.S. Pat. No. 3,499,591 to Green, which is incorporated herein by reference, applies a double row of staples on each side of the incision. This is accomplished by a cartridge assembly wherein a cam member moves within an elongate guide path between two sets of staggered staple carrying grooves. Staple drive members are positioned in such a manner so as to be contacted by the longitudinally moving cam to effect ejection of the staples. The cartridge assemblies typically come in a plurality of sizes, each varying in both length and number of staples contained therein. Depending on the procedure to be performed, the surgeon must select the appropriate cartridge assembly.

The instruments described above were all designed for use in surgical procedures wherein surgeons have direct access to the operation site. However, in endoscopic or laparoscopic procedures, surgery is performed through a small incision or through narrow cannulae inserted through entrance incisions in the skin. In order to address the specific needs of endoscopic and/or laparoscopic surgical procedures, endoscopic surgical stapling devices such as those disclosed in U.S. Pat. No. 5,040,715 and U.S. Pat. No. 5,318,221, both to Green et al., have been developed. In general, these instruments are provided with clamping structure to effect approximation of an anvil and a staple cartridge to secure tissue therebetween, and staple firing structure to effect sequential ejection of a plurality of staples from the staple cartridge after the tissue has been secured.

It is the case with most prior art stapling instruments designed to sequentially place one or more lines of staples on both sides of an incision, that once the profile of the device is undesirably large. As the instrument is inserted within the body, the larger the device, the larger the typical damage. This can complicate the surgical procedure and add to the recovery time.

While prior art stapling and cutting instruments have proven useful, it would be beneficial to provide a surgeon with an instrument that is small and provide control over staple placement along an incision during an endoscopic surgical procedure so as to alleviate the problems associated with relatively larger stapling instruments.

SUMMARY OF THE INVENTION

In one embodiment, the subject disclosure is directed to a fastening and cutting assembly for an instrument that staples and cuts body tissue. The assembly has a housing defining an axial passage and a pusher slidably received in the axial passage. The pusher has a cam surface. An arm couples to the housing and an anvil base is located on the arm. A cartridge body slidably mounts on the arm between the housing and the base. The cartridge body defines an axial bore and a staple passage. A cam follower extends from the cartridge body to the housing. A knife blade couples to the pusher for movement in the axial bore. A staple is in the staple passage. In an open position, tissue can be placed between the anvil base and the cartridge body. In an intermediate position, the cam surface of the pusher can move the cam follower into a locked position and, thereby, the tissue can be clamped between the cartridge body and the anvil base. In a fastened and cut position, the primary pusher can move such that the staple can be been driven and formed in the tissue and the knife blade can cut the tissue against the anvil base.

In another embodiment, the subject disclosure is directed to an instrument for stapling and cutting body tissue including a handle portion for actuating and controlling placement of the instrument. A pusher housing has a proximal end coupled to the handle portion and defines a pusher axial passage having a hollow. A primary pusher is slidably received in the pusher axial passage. The primary pusher has a cam surface. An anvil assembly has an arm coupling to the pusher housing and a base located on a distal end of the arm. A cartridge body 140 slidably mounts on the arm, the body including a distal face and a proximal face. The cartridge body defines an axial bore and at least one staple passage. A cam follower extends from the proximal face. A knife blade couples to the primary pusher for sliding movement in the axial bore and at least one staple is in the at least one axial staple passage. In an open position, the handle portion is used to place tissue in between the anvil base and the distal face of the cartridge body. In an intermediate position, the handle portion has actuated the primary pusher such that the cam surface has moved the cam follower into a locked position in the hollow and, thereby, the tissue is clamped. In a fastened and cut position, the handle portion has further actuated the primary pusher such that the staple has been driven and formed in the tissue and the knife blade has cut the tissue against the anvil base.

Another embodiment is directed to an instrument for stapling and cutting body tissue having a handle portion for actuating and controlling placement of the instrument with an elongated pusher housing having a proximal end coupled to the handle portion. The pusher housing defines a locking passage and a pusher axial passage having a hollow. A primary pusher is slidably received in the pusher axial passage, the primary pusher being a plate with a closer cam block and a release cam block upstanding therefrom. A cartridge assembly couples to the pusher housing. The cartridge assembly includes a body with a distal face and a proximal face. A cam follower extends from the proximal face, the body defining an axial bore, two opposing axial staple passages and opposing staple load passages. An anvil assembly has an arm extending through the axial bore and coupled to the locking passage. The anvil assembly also has a base located on a distal end of the arm wherein a proximal face of the base forms a tissue gap with the distal face of the body. A knife blade is coupled to the primary pusher for sliding movement in the axial bore. A first secondary pusher is coupled to the primary pusher for sliding movement in one of the axial staple passages and a second secondary pusher is coupled to the primary pusher for sliding movement in the other of the axial staple passages. Staples are in the axial staple passages. In a normally open position, the handle portion is used to place tissue in the tissue gap. In an intermediate position, the handle portion has actuated the primary pusher such that the closer cam block has moved the cam follower such that the cam follower is locked in the hollow to clamp the tissue. In a fastened and cut position, the handle portion has further actuated the primary pusher such that the first and secondary pushers have each driven and formed a staple in the tissue and the knife blade has cut the tissue.

In another embodiment, the subject technology is directed to a cartridge assembly for a surgical fastening and cutting instrument. The cartridge assembly includes a cartridge body including a distal face and a proximal face, the body defining an axial bore and at least one staple passage and a flexible cam follower extending from the proximal face and having a cam surface.

It should be appreciated that the present invention can be implemented and utilized in numerous ways, including without limitation as a process, an apparatus, a system, a device, and a method for applications now known and later developed. These and other unique features of the system disclosed herein will become more readily apparent from the following description and the accompanying drawings.

BRIEF DESCRIPTION OF THE DRAWINGS

So that those having ordinary skill in the art to which the surgical apparatus and method of the subject invention appertains will more readily understand how to make and use the same, reference may be had to the following drawings.

FIG. 8 is a perspective view, in partial cross-section, of the fastening and cutting assembly in the open position, as viewed from a distal end thereof.

FIG. 9 is a perspective view, in partial cross-section, of the fastening and cutting assembly, in the open position, as viewed from a proximal end thereof.

FIG. 15 is a perspective view of the fastening and cutting assembly of the surgical instrument of FIG. 1, with the body of the staple cartridge having moved to capture tissue against the anvil base.

FIG. 16 is a side cross-sectional view showing the engagement of the closer cam block of the primary pusher to the cam follower during activation from the open position to the closed position.

FIG. 17 is a side cross-sectional view of the surgical instrument, taken along line 17-17 of FIG. 15, showing the position of the cam follower in the closed position with captured tissue in the intermediate position.

FIG. 18 is an enlarged perspective view of the circle labeled 18 in FIG. 15, showing the cam follower with the fastening and cutting assembly gripping tissue in the intermediate position prior to stapling and cutting.

DETAILED DESCRIPTION OF PREFERRED EMBODIMENTS

Figure 1:
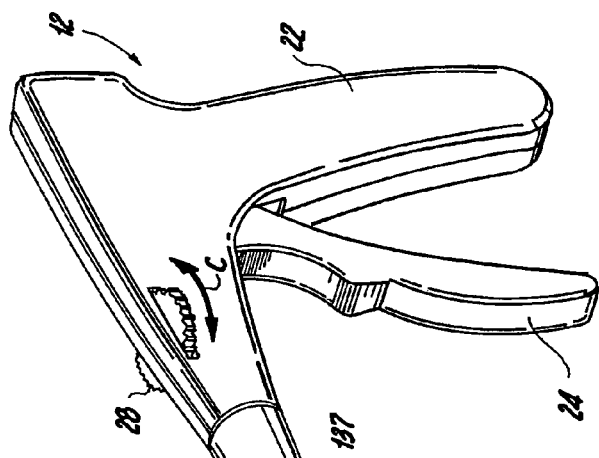
FIG. 1 is a perspective view of a surgical cutting and stapling instrument constructed in accordance with the present disclosure, with the fastening and cutting assembly oriented in an open position.

The present invention overcomes many of the prior art problems associated with endoscopic and laparoscopic stapling instruments. The advantages, and other features of the instrument disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

It is generally accepted that the technology of endoscopic procedures is interchangeable with laparoscopic procedures. The following embodiments may be discussed in terms of one procedure but it is equally applicable to either or any equivalent procedure now known or later developed. Thus, use herein of such terms such should not be construed to limit the claims appended hereto to a cutting and stapling instrument for use only in conjunction with an endoscopic or laparoscopic tube. On the contrary, it is believed that the embodiments described herein may find use in any procedure where access is a small incision. Also, as used herein the terms "fasteners" and "staples" shall be treated equivalently. Unless otherwise stated, the term "cartridge assembly" shall include at least the cartridge itself and staples or fasteners and staple drive members disposed therein. In the drawings and the description which follows, as is customary, the term "proximal" refers to the end which is closest to the operator when the instrument is in use, while the term "distal" will refer to the end which is furthest from the operator during use thereof. All relative descriptions herein such as above, below, left, right, up, and down are with reference to the Figures, and not meant in a limiting sense.

Following is a detailed description of the present instrument. The description is divided into separate sections to describe the structure and the desired movements produced thereby. Those sections include the instrument, the handle section, the fastening and cutting assembly, loading the instrument, using the instrument, and the safety lock. The following description is in reference to the drawings, wherein like reference numerals designate corresponding parts throughout the several views.

I. The Instrument

Referring initially to FIG. 1, there is illustrated in perspective view the instrument 10 particularly adapted for cutting and applying surgical staples to body tissue. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) may also be utilized. However, equivalent alternative materials now known and later developed will readily come to the mind of those skilled in the art.

The instrument 10, as noted above, is configured to cut and fasten body tissue. The instrument 10 can progressively apply a plurality of surgical fasteners or staples to the tissue, while progressively forming an incision in the fastened body tissue during a surgical procedure. In brief overview, the instrument 10 includes a handle portion 12 for controlling and actuating the instrument 10. An elongated intermediate portion 14 extends distally from the handle portion 12 and defines a longitudinal axis. A fastening and cutting assembly 16 is supported on the distal end of the elongated intermediate portion 14.

Figure 5:
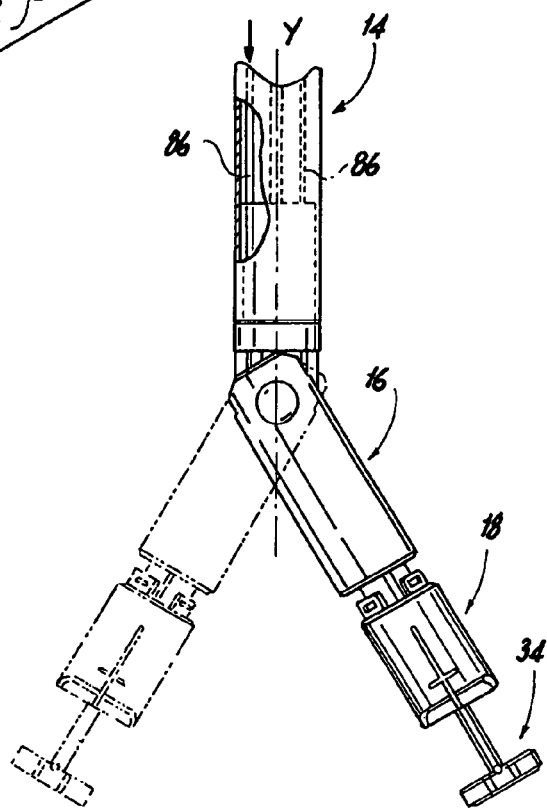
FIG. 5 is a top view of the distal portion of the surgical instrument of FIG. 1 in articulated positions relative to the axis of the instrument body.

When loaded with a staple cartridge assembly 18, the fastening and cutting assembly 16 is positioned by a steering knuckle assembly or joint 20 between the fastening and cutting assembly 16 and the intermediate portion 14. The steering knuckle joint 20 allows an articulating motion of the fastening and cutting assembly 16 about an axis "x" extending perpendicular to the longitudinal axis of the intermediate portion 14 through an arc denoted by arrow "a" and also as shown in FIG. 5. The elongated intermediate portion 14 is generally tubular to allow various cables, rods and the like to extend therethrough.

Referring still to FIG. 1, the handle portion 12 of the instrument 10 includes a stationary manual grip 22 and a pivotable trigger 24 which is mounted to be pivoted toward and away from the manual grip 22. The trigger 24 is pivoted toward the manual grip 22 as described in further detail below to activate a firing linkage assembly 26 (see FIGS. 3, 4 and 7-9) and thereby start the cutting and stapling sequence, e.g., movement in the direction along arrow "b" of the staple cartridge assembly 18. After firing, the trigger 24 pivots away from manual grip 22 to return the instrument 10 to the prefired position or open position for further stapling and cutting.

A manually operative ratcheting star wheel 28 is rotatable, about an axis denoted by arrow "c", to control the position of steering knuckle assembly 20. The star wheel 28 is conveniently positioned within the handle portion 12 to permit access by a user's fingers. In another embodiment, the handle portion 12 forms a relief for minimizing accidental rotation of the star wheel 28. Upon using the handle portion 12 and star wheel 28 to position the fastening and cutting assembly 16 in the desired location relative to the intermediate portion 14, the trigger 24 is actuated to fire the instrument 10, as discussed in greater detail below.

Figure 2:
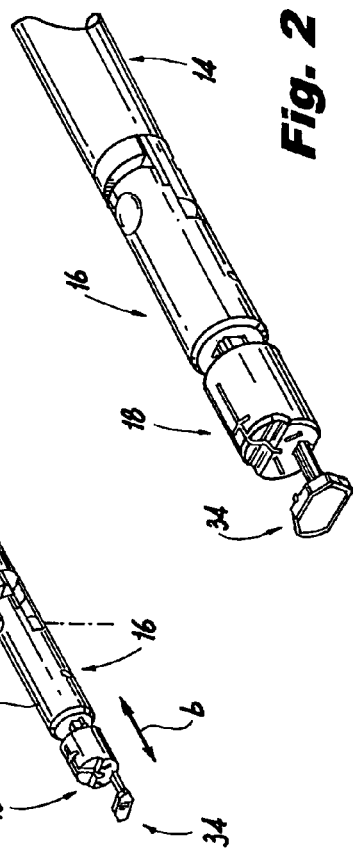
FIG. 2 is a detailed perspective view of the fastening and cutting assembly of FIG. 1.

Referring to FIG. 2, the fastening and cutting assembly 16 houses the staple cartridge assembly 18 in a removable manner. In the normally biased open position, the staple cartridge assembly 18 can be manually inserted or removed to make sure ample staples 128 (see FIG. 7) are ready for the surgical procedure. When the instrument 10 is actuated, a distal face 19 of the staple cartridge assembly 18 drives against an anvil assembly 34 to form the incision and staples 128. Structure to accomplish driving the staple cartridge assembly 18 against the stapler anvil assembly 34 and forming an incision in the stapled tissue is provided. It is envisioned that many types of driving linkages would perform adequately within the subject instrument.

II. The Handle Section

Figure 3:
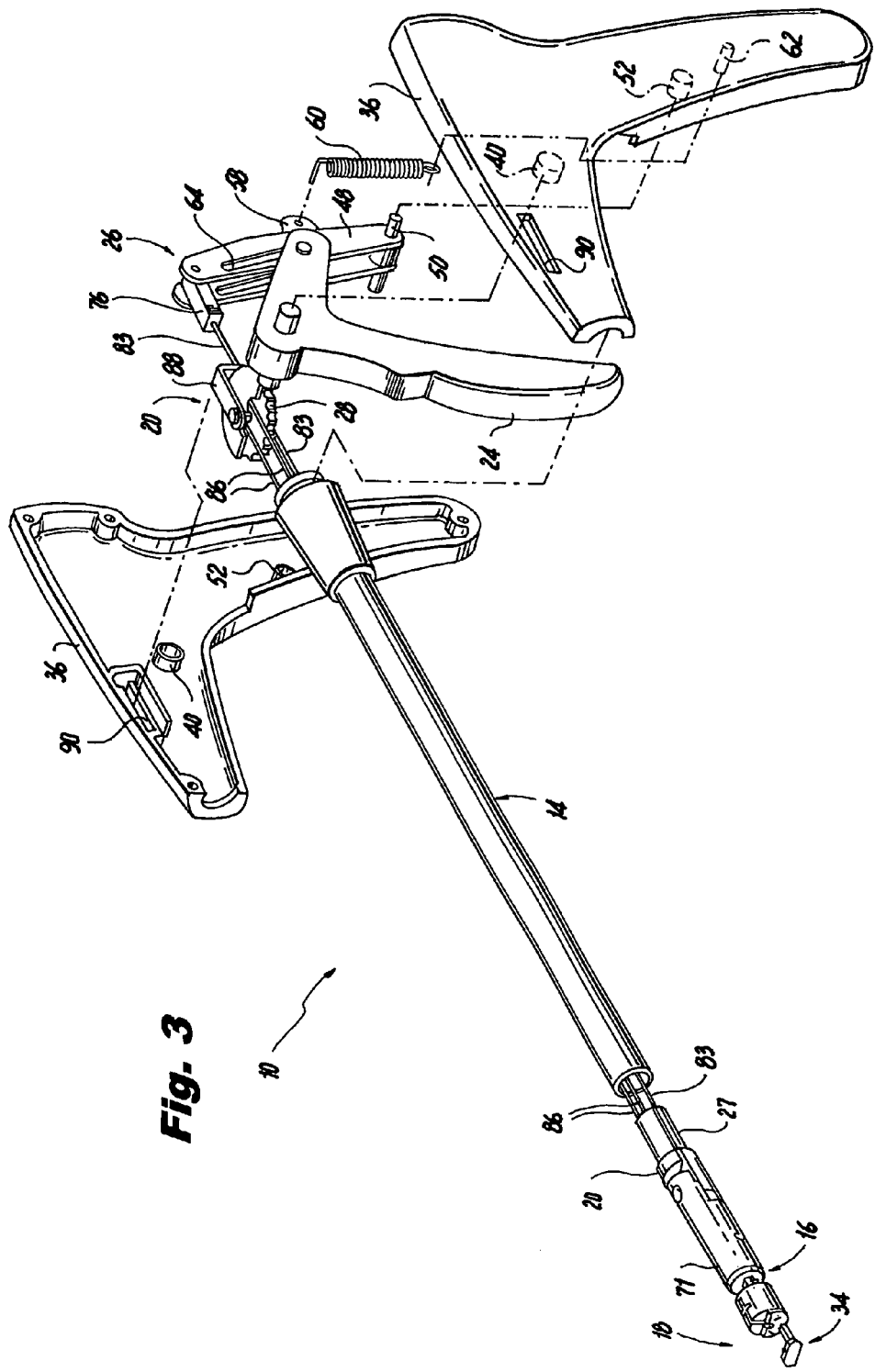
FIG. 3 is an exploded perspective view with parts of the handle portion separated.
Figure 4:
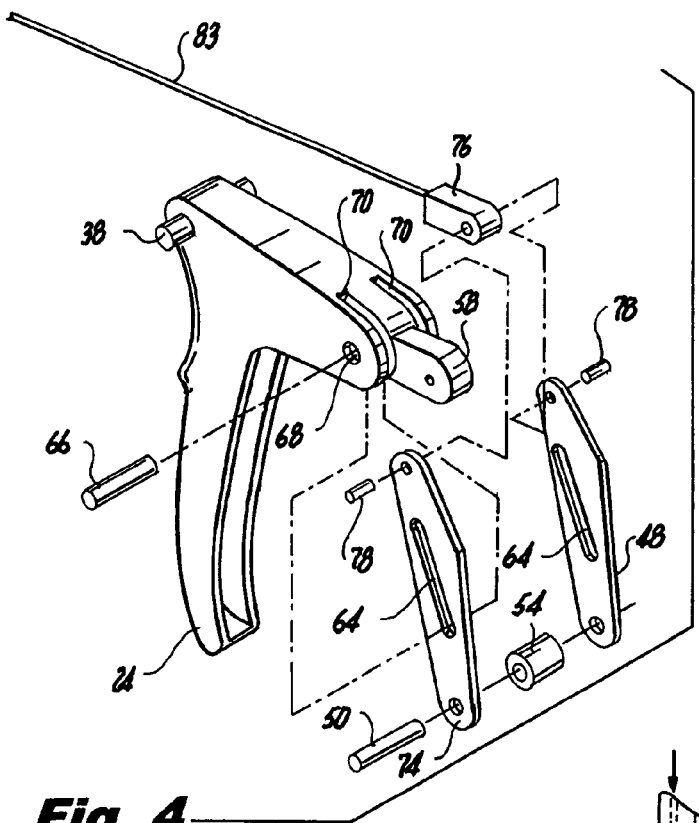
FIG. 4 is an exploded perspective view of the firing linkage assembly of the surgical instrument of FIG. 1.

Referring now to FIGS. 3 and 4, there are shown two perspective views of the handle portion 12 with parts separated for illustration purposes. The handle portion 12 allows a user to position the instrument 10 and control both the steering assembly and instrument firing. The handle portion 12 is comprised of a two-piece handle 36 preferably formed of polycarbonate material. The separate parts of the handle portion 12 and other components of the instrument 10 may be attached by interference fit, welding, adhesives, screws and the like. The ultimate purpose of the handle portion 12 is to provide controlled movement of the fastening and cutting assembly 16. The trigger 24 is pivotally mounted to the handle 36 by pivot pin 38. Opposing bosses 40 on the inside of the handle 36 capture each side of the pivot pin 38. The trigger 24 is roughly L-shaped to translate force to drive the firing linkage assembly 26.

The firing linkage assembly 26 has a cam portion 48 driven by the trigger 24. The cam portion 48 pivots at a lower end about a pin 50 received in shoulders 52 formed in the handle 36. A bushing 54 allows independent rotation thereof. A rearward projection 58 on the trigger 24 passes intermediate the cam portion 48 and connects to a spring 60, which extends to a retaining post 62 of the handle 36. The trigger 24 is biased by the spring 60 to the open position.

The cam portion 48 forms a cam track 64, respectively, for slidably receiving a cam pin 66 captured in a transverse bore 68 of the trigger 24. The cam portion 48 slides into respective slots 70 formed in the trigger 24. In the open position, the cam pin 66 is preferably at the bottom of the cam track 64. The cam track 64 is shaped to achieve the desired results described in more detail below. In a preferred embodiment, the cam track 64 has two offset linear sections as shown in U.S. patent application Ser. No. 11/410,346 filed Apr. 25, 2006, which is incorporated herein by reference. The cam tracks can be configured to move independently and vary the tensioning and timing of translated movement as desired to accomplish proper actuation.

A swing block 76 pivotally mounts to the top of the cam portion 48 by pins 78. The swing block 76 also retains a push-rod 83. As described hereinbelow, actuation of the trigger 24 causes proximal movement of the cam portion 48 such that the push-rod 83 is selectively urged distally or retracted to fire the instrument (e.g., capture, cut and staple tissue). As can be seen, the firing linkage assembly 26 serves to translate force from the trigger 24 to the fastening and cutting assembly 16 and, as such, many means for this function would be apparent to those of ordinary skill in the art based upon review of the subject disclosure.

In one embodiment, the proximal portion of the intermediate portion 14 is rotatably mounted to the handle portion 12 to facilitate axial rotation of the fastening and cutting assembly 16 relative to the handle portion 12. A hub 137 rotatably connects the handle portion 12 and the intermediate portion 14 for rotational adjustment.

Referring to FIG. 3, the steering knuckle assembly 20 includes the manually adjustable star wheel 28 mounted on the handle 36 and connected by a steering rod 86 to a steering pin 29. In another embodiment, one or more cables is used instead of a steering rod 86. The steering knuckle assembly 20 allows the user to vary and set the angular relationship between the fastening and cutting assembly 16 and the elongated intermediate portion 14 such that further manipulation is not required. As a result, the user can pay undivided attention to locating and firing the instrument 10. FIG. 5 shows the steering knuckle assembly 20 having moved the fastening and cutting assembly 16 out of alignment with the intermediate portion 14 and in phantom lines to illustrate a second possible position out of alignment with the axis "y".

Figure 7:
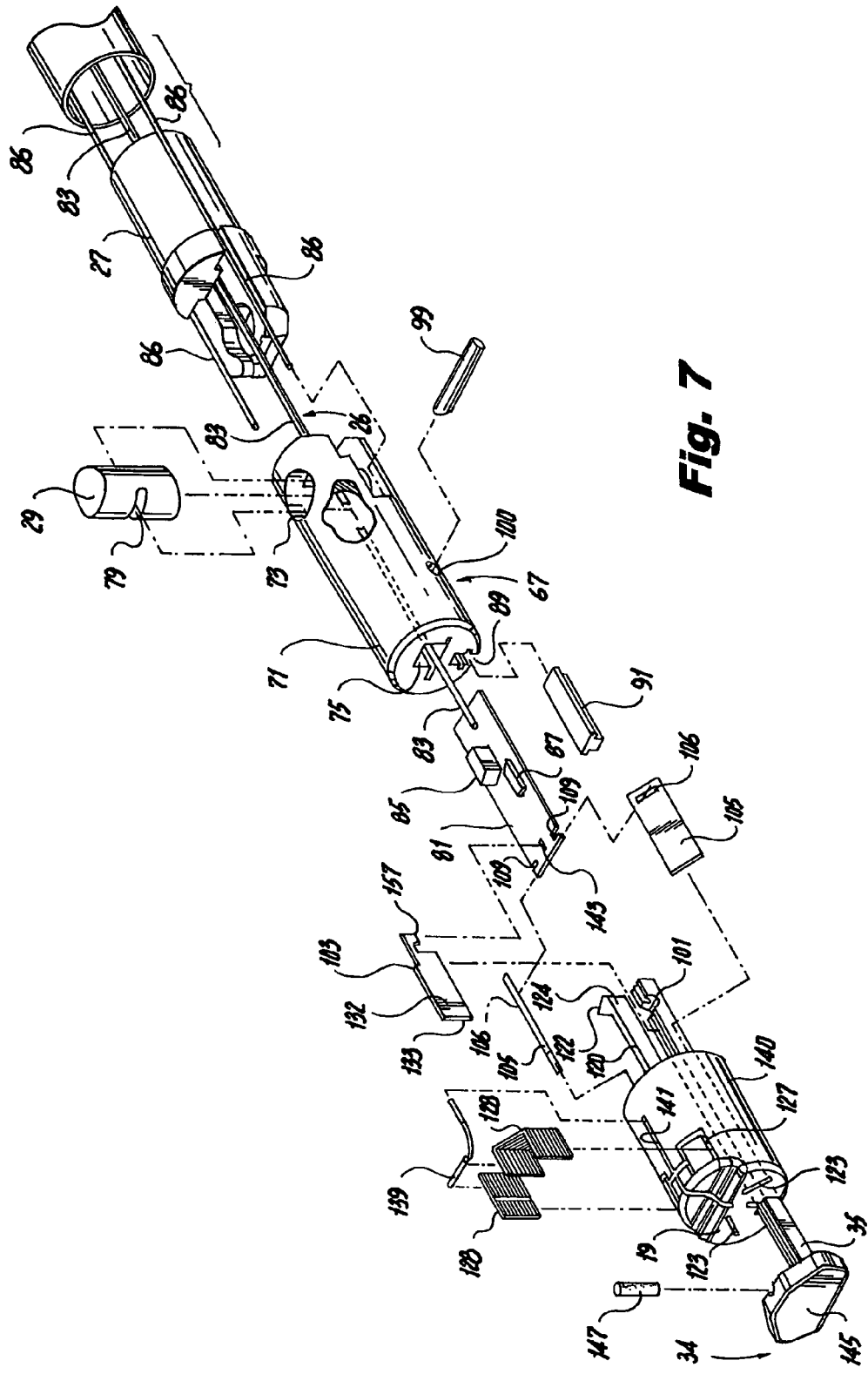
FIG. 7 is an exploded perspective view of the fastening and cutting assembly of FIG. 6, with parts separated for ease of illustration.
Figure 10:
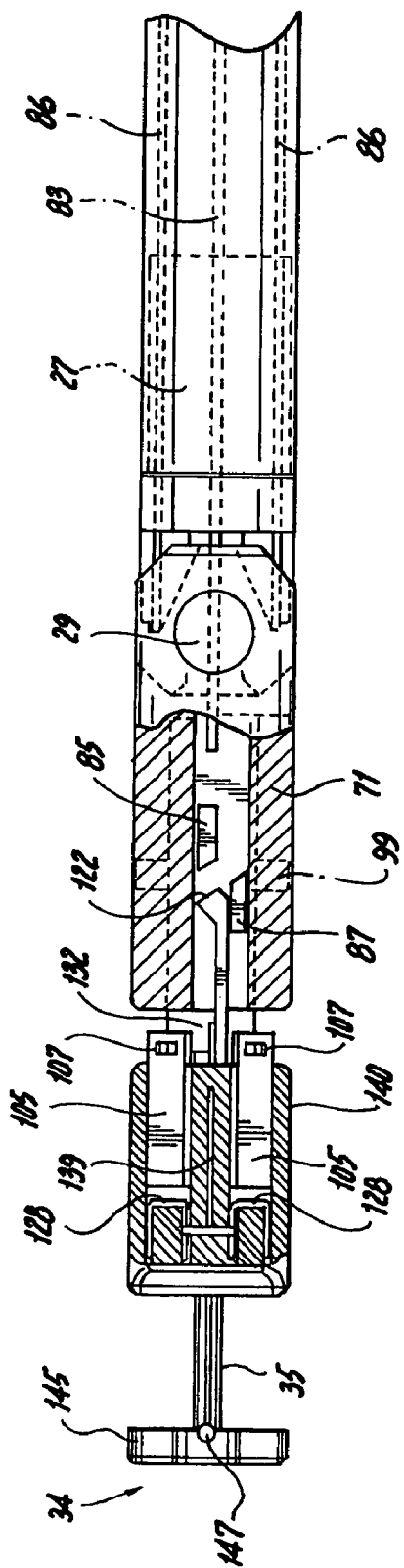
FIG. 10 is a top view of the fastening and cutting assembly of the instrument of FIG. 1, in cross-section to reveal the internal components.
Figure 11:
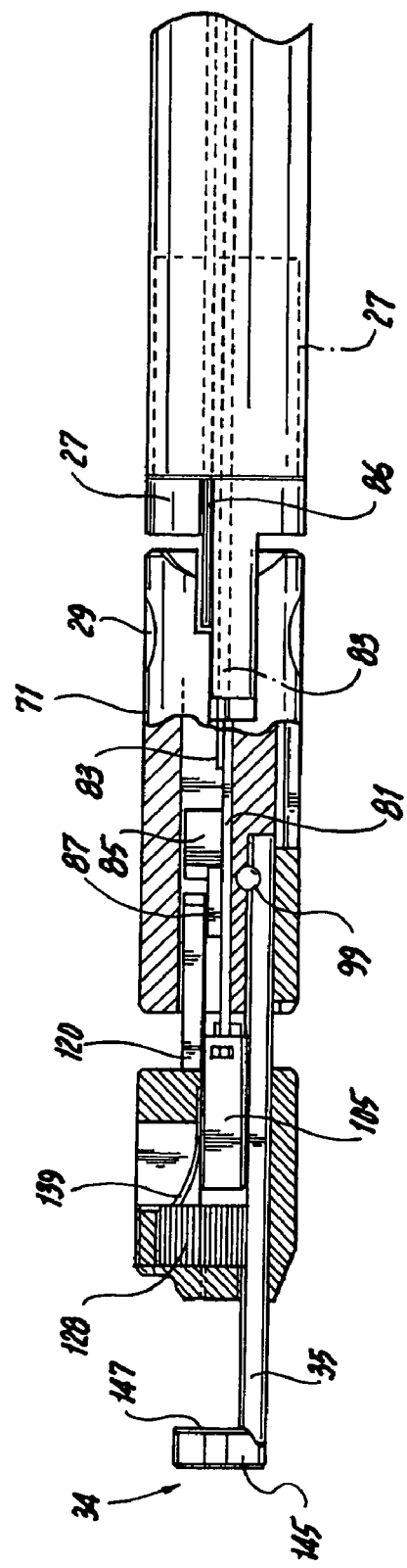
FIG. 11 is a side elevational view of the surgical instrument of FIG. 10 in cross-section to reveal the internal components of the fastening and cutting assembly.

Referring to FIGS. 3 and 5, the handle 36 secures a bracket 88 having the star wheel 28 rotatably mounted thereon. Apertures 90 on opposing sides of the handle 36 allow the star wheel 28 to protrude from the handle 36 and, thereby, be accessed by the user. The star wheel 28 acts as a pusher coupled to the steering rod 86. The steering rod 86 forms an elongated loop about the steering knuckle 27 at one end and about the star wheel 28 at the other end. Referring now also to FIGS. 7-9, the steering rod 86 passes through the elongated intermediate portion 14 without obstruction such that rotation of the star wheel 28 causes a corresponding rotation of the steering knuckle 27 and the fastening and stapling assembly 26 coupled thereto.

III. The Fastening and Cutting Assembly

Referring to FIGS. 1 and 7, the fastening and cutting assembly 26 has two major sub-assemblies, the staple cartridge assembly 18 and the pusher housing assembly 67. The pusher housing assembly 67 interacts with and extends from the steering knuckle 27. The staple cartridge assembly 18 interacts with and extends from the pusher housing assembly 67. The pusher housing assembly 67 drives the components of the staple cartridge assembly 18 to capture, incise and staple tissue.

A. The Pusher Housing Assembly

Referring to FIG. 7, there is shown a perspective view, with parts separated for illustration purposes, of the pusher housing assembly 67 of the instrument 10. The pusher housing assembly 67 has a pusher housing 71 that forms a transverse bore 73 intersecting with an axial passage 75. The transverse bore 73 retains the steering pin 73. Steering rod 86 passes into the axial passage 75 to loop around a groove 79 formed in the steering pin 29. As the steering rod 86 loops in an arcuate pocket extending through the star wheel 28 such that upon rotation of the star wheel 28, the pusher housing assembly 67 and, thereby, the staple cartridge assembly 18 selectively rotate as shown in FIG. 5.

The pusher housing assembly 67 also includes a primary pusher 81 that slides within the axial passage 75 from the proximal end. The primary pusher 81 is a plate 82 with closer cam block 85 and a release cam block 87 mounted thereon. The primary pusher 67 is moved by the firing linkage assembly 26. A push-rod 83 of the firing linkage assembly 26 extends from the handle 12 to attach to a proximal end of the primary pusher 81. The push-rod 83 may be a solid rod, a rigid wire, a tube or a multi-piece construction. In one embodiment, the push-rod 83 is mostly a solid rod to provide excellent force transfer with a wire portion welded in near from the steering knuckle 27 to the primary pusher 81 to provide flexibility in the region of the steering pin 29.

B. The Staple Cartridge

Figure 6:
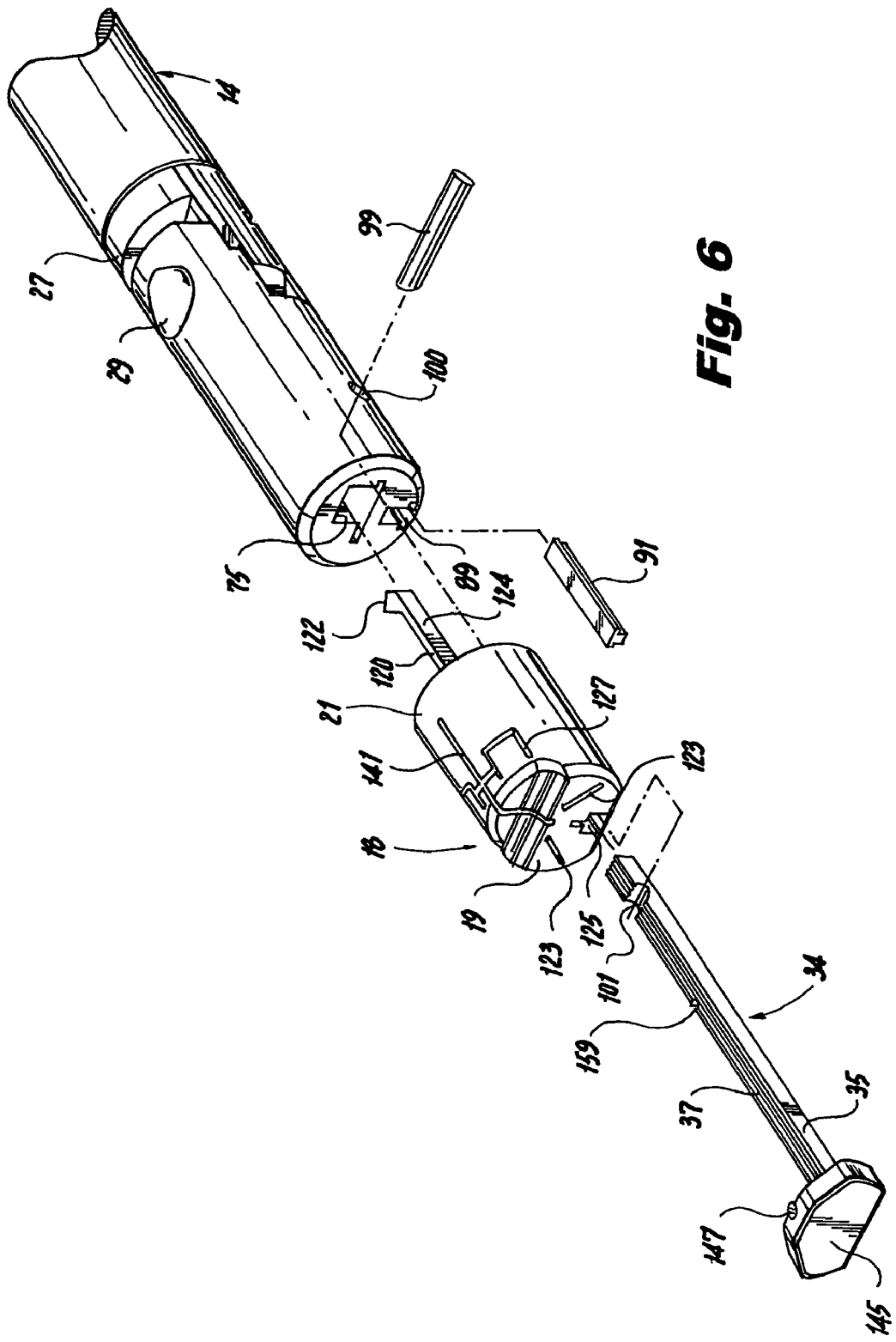
FIG. 6 is a partially exploded perspective view of the staple cartridge assembly of the fastening and cutting assembly of the instrument of FIG. 1.

Referring now to FIGS. 6 and 7, there are shown two perspective views of the instrument 10 with parts separated for illustration purposes and, in particular, the components of the staple cartridge assembly 18 exploded. The staple cartridge assembly 18 retains a plurality of staples 128, in two rows, for deployment in tissue as well as a knife 132 for cutting tissue. As described hereinabove, the staple cartridge assembly 18, when assembled, is inserted or loaded into the fastening and cutting assembly 16. It is envisioned that one or more staple cartridges 18 may be provided with the instrument 10. The staple cartridge assembly 18 may be disposable or sterilized and re-loaded with additional staples 128 for re-use.

The staple cartridge assembly 18 has a body 140 that supports and guides the various components. The body 140 is rod-shaped with a distal face 19 and a proximal face 21. Two axial staple passages 123 and a knife slot 125 run axially through the distal face 19. Transverse passages 127 allow loading the staples 128 into the body 140. The staples 128 are roughly U-shaped but various configurations may be accommodated.

Figure 25:
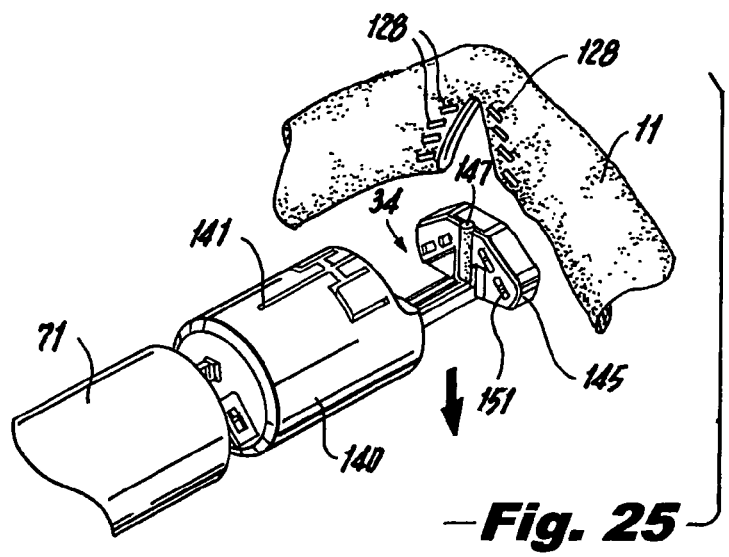
FIG. 25 is a perspective view of the stapling and cutting assembly of the surgical instrument of FIG. 1, as the surgical instrument is being withdrawn from a surgical site wherein two staples have been applied to body tissue that has been substantially simultaneously cut.

The axial staple passages 123 are preferably offset with respect to the tissue incision (see FIG. 25). However, the staples 128 could also be set perpendicular and/or parallel to the tissue incision. Similarly, a single staple 128 or multiple staples may be secured adjacent the incision as desired for specific applications. In one embodiment, the rows of staples 128 are joined by an adhesive and, in another embodiment, each staple 128 is individually loaded into the load passages 127. The staples 128 are biased to the distal most position in the axial passages 123 by a staple tensioner spring 139. The staple tensioner spring 139 is disposed a transverse T-shaped slot 141 in the body 140.

The axial bore 125 of the body 140 also receives an anvil assembly 34. The anvil assembly 34 provides a surface for the knife blade 132 to cut the tissue against in the form of an anvil base 145 with a rod 147. The anvil assembly 34 has an arm 35 extending proximally from the anvil base 145. The arm 35 extends through the axial bore 125 and into a locking passage 89 formed in the pusher housing 71. An anvil lock 91 and anvil pin 99 secure the anvil arm 35 to the pusher housing 71. The anvil lock 91 couples with the anvil arm 35 in the locking passage 89. To further secure the anvil assembly 34, an anvil pin 99 passes through a hole 100 in the pusher housing 71 to engage a groove 101 formed in the anvil arm 35. As a result, the staple cartridge body 140 slidably mounts on the anvil arm 35 but the relationship between the anvil assembly 34 and the pusher housing 71 is fixed.

Figure 26:
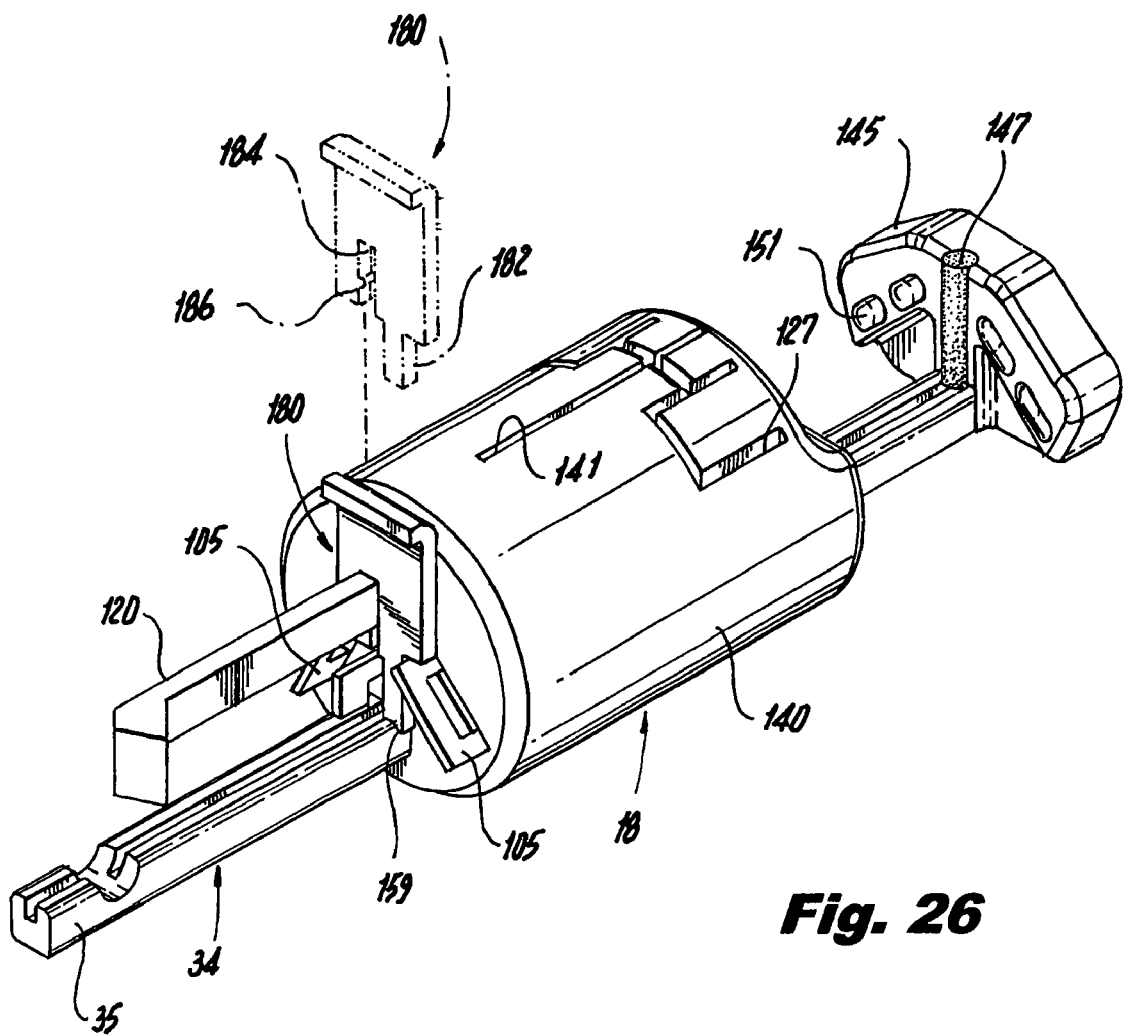
FIG. 26 a perspective view of a safety lock in place on a staple cartridge assembly.

A knife blade 132 slidably moves within the axial bore 125 of the body 140 of the staple cartridge assembly 18. A knife channel 37 formed in the anvil arm 35 guides the knife blade 132 so that a razor sharp distal edge 133 of the knife blade 132 cuts tissue against the rod 147 as described below. The knife blade 132 couples to the primary pusher 81 by a projection 157 formed in the proximal end. The projection 157 is captured within a slot 143 formed on the distal end of the primary pusher 81. The knife blade 132 has an upper notch 103 to engage and retract the body 140 toward the handle portion 12. As best seen in FIG. 26, the axial bore 125 at the proximal face 21 of the body 140 is sized and configured to allow the projection 157 of the knife blade 132 to extend out but not the portion of the knife blade 132 distally past the upper notch 103. As a result, the upper notch 103 affirmatively catches on the body 140 so that upon the primary pusher 81 being retracted, the knife blade 132 and body 140 are similarly retracted.

Secondary pushers 105 axially slide in the axial staple passages 127, respectively, for providing the force on the staples 128 to form the staples 128. The secondary pushers 105 define slots 107 that are captured by projections 109, respectively, of the primary pusher 81. As a result, when the primary pusher 81 moves, the secondary pushers 105 move similarly.

A cam follower 120 extends from the proximal face 21 of the body 140. The cam follower 120 is a flexible member that terminates in cam surfaces 122, 124. The cam surfaces 122, 124 interact with the cam blocks 85, 87 of the primary pusher 81 to set and transition between the various operational positions.

Referring to FIGS. 1-7, it can be seen that the handle 12 and star wheel 28 are used to position the fastening and cutting assembly 16. Upon proper placement, force applied to the trigger 24 is transmitted to the fastening and cutting assembly 16 to activate the instrument 10 resulting in an incision with staples 128 formed adjacent thereto.

IV. Loading the Instrument

Referring in particular to FIGS. 8-11, various views of a loaded instrument 10, in the open position, are shown cut-away to illustrate the relationship between the components. As the mechanical structure and connections have been described above, preparation of the instrument for use will now briefly be described.

The staple cartridge assembly 18 has stacks of staples 128 loaded into the staple load passages 127. The staples 128 can be loaded into the passages 127 as necessary or the entire staple cartridge assembly 18 can be removed replaced for subsequent use.

It is envisioned that the staple cartridge assembly 18 and/or the instrument 10 may be preloaded by a machine as would be known to those of ordinary skill in the art or manually loaded in a sterile environment. In one embodiment, the instrument 10 comes loaded with a single staple cartridge assembly 18 and is entirely disposable. It is also contemplated that the fastening and cutting assembly 16 is selectively detachable at the steering knuckle 27 so that the handle portion 12 may be sterilized and reused with a new fastening and cutting assembly 16. Alternatively just the staple cartridge assembly 18 is disposable.

Once the instrument 10 is loaded, the staple cartridge assembly 18 is put in the open position. In the open position, the tissue gap 149 between the proximal side of the anvil base 145 and the distal face 19 of the body 140 is at or very near a maximum. Because of the connection to the trigger 24, which is normally biased open, the primary pusher 81, knife blade 132, body 140 and secondary pushers 105 are all retracted. The cam surfaces 122, 124 of the cam follower 120 are separated from the cam blocks 85, 87 of the primary pusher 81.

V. Using the Instrument

The application of the instrument 10 to staple and cut a portion of body tissue will now be described sequentially. Initially, the instrument 10 is readied for use by loading staples 128 and/or a staple cartridge assembly 18. If the safety lock 180 is present, the safety lock 180 is removed. The trigger 24 of the handle portion 12 is not depressed so the instrument 10 is in the open position.

A. Locating the Instrument

Figure 12:
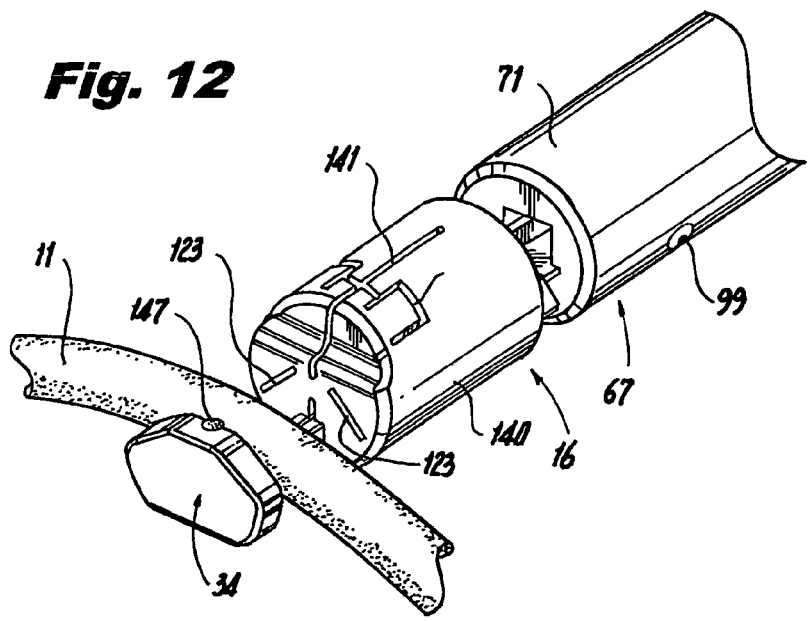
FIG. 12 is a perspective view of the fastening and cutting assembly of the surgical instrument of FIG. 1, in the open position with tissue being in the tissue gap.
Figure 13:
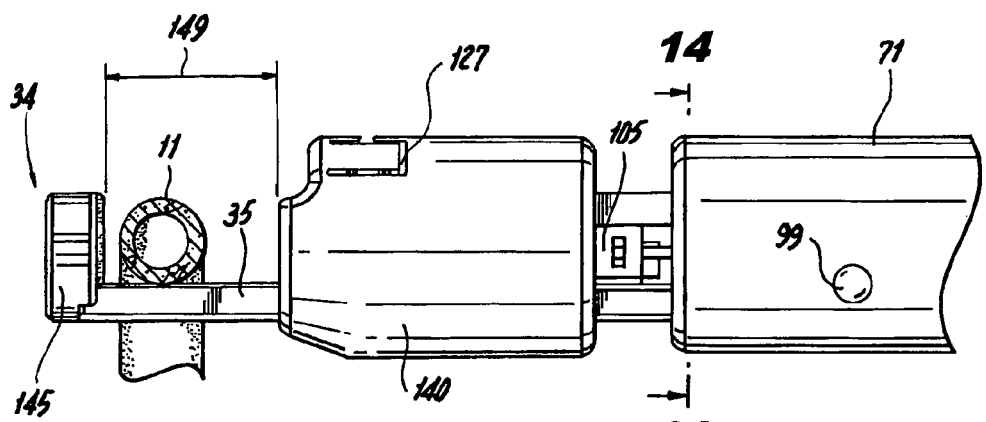
FIG. 13 is a side elevational view of the surgical instrument of FIG. 12.
Figure 14:
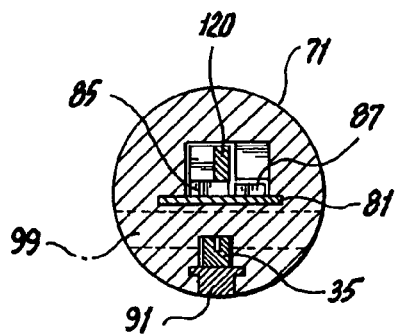
FIG. 14 is a sectional view taken along lines 14-14 of FIG. 13, which shows a cam follower in a pre-tissue capture position.

Referring now to FIGS. 12-14, a perspective view, a side view and a cross-sectional view, respectively, of the fastening and cutting assembly 16 are shown with tissue 11 initially placed on the anvil assembly 34. The intermediate portion 14 is sized to allow entering through an incision and placement of the fastening and cutting assembly 16 at the operable site while allowing the surgeon to control usage with the handle portion 12 from a comfortable distance and position. By spinning the star wheel 28, the steering knuckle assembly 20 is used to orient the fastening and cutting assembly 16 as desired.

In the open position, the surgeon uses the handle portion 12 to guide the tissue 11 into position between the proximal face 146 of the anvil base 145 and the distal face 19 of the body 140. The tissue gap 149 or distance between the proximal face 146 and distal face 19 is preferably 0.30 inches for an instrument 10 having an approximately nine millimeter diameter body 140. As can be seen in FIGS. 8-11 and 14, the cam follower 120 and the primary pusher 81 are largely extending into the pusher housing 71 but the only contact between the cam blocks 85, 87 and the cam follower 120 is the cam surface 124 resting against the closer cam block 87.

B. Closing the Tissue Gap to Capture the Tissue

Referring to FIGS. 15-18, various views of the fastening and cutting assembly 16 being driven to close the tissue gap 149 and capture the tissue 11 are shown. Upon placement of the desired tissue 11 in the tissue gap 149, the trigger 24 is squeezed to move the body 140 toward the anvil base 145 and positively lock the tissue 11 in the reduced tissue gap 149. The force upon the trigger 24 is transmitted through the firing linkage assembly 26 to the push-rod 83. The push-rod 83 urges the primary pusher 81 in a distal direction denoted by arrows "c" and, thereby, the knife blade 132 and secondary pushers 105 move distally as well.

As the primary pusher 81 moves along arrows "c", the closer cam block 85 contacts the cam surface 122 of the cam follower 120 as shown in FIG. 16. As the cam follower 120 snugly fits in the locking passage 89, the movement of the closer cam block 85 is efficiently transferred to the cam follower 120 and, thereby, the body 140 begins to move toward the anvil base 145. Thus, the tissue 11 is captured in the tissue gap 149. Preferably, only a small area of the tissue 11 is captured so that a force of about 8 or 9 lbs provides sufficient retentive force.

Referring in particular to FIGS. 17 and 18, the closer cam block 85 engages the cam surface 122 of the cam follower 120 until the proximal end 121 of the cam follower 120 toggles into a hollow 93 formed in the pusher axial passage 75. In this intermediate position, the cam follower 120 is flexed to provide positive holding force, i.e., capture the tissue 11, independent of force provided from the trigger 24. Consequently, there is an initial pressure provided by the trigger 24 to capture the tissue 11, but once captured subsequent forces are not needed to maintain the positive holding of the tissue 11.

Once in the intermediate position, the primary pusher 81 continues driving into the body 140 of the staple cartridge assembly 18 so that each secondary pusher 105 contacts a bottom staple 128 and begins to push these bottom staples 128 toward the tissue. The knife blade 132 is also driven towards the tissue 11.

C. Cutting and Stapling the Tissue

Figure 19:
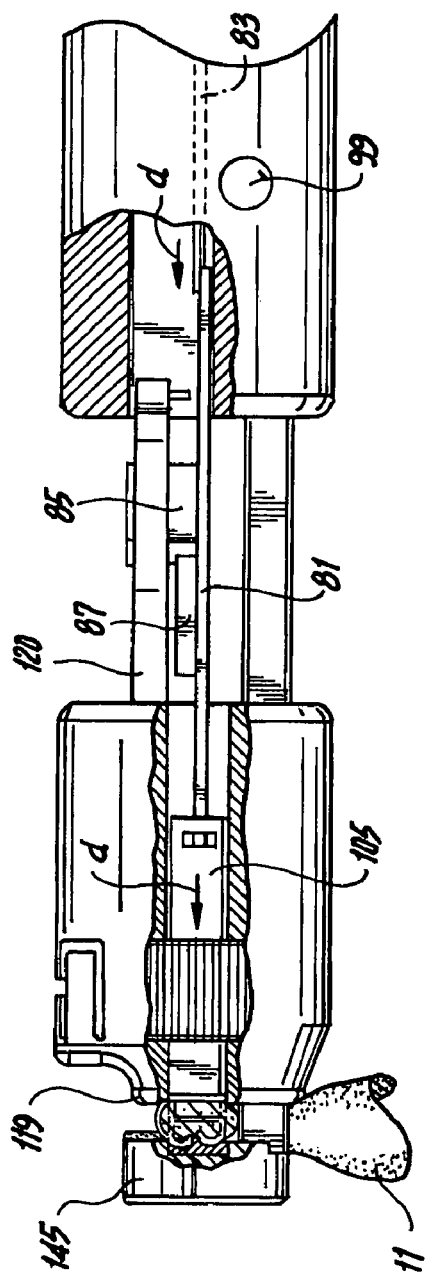
FIG. 19 an enlarged side view, in cross-section, of the fastening and cutting assembly of the surgical instrument, with the primary staple pusher moved toward the anvil base such that the staples are driven through the tissue and formed in the cups of the anvil base and the knife blade rests against the rod after forming an incision in the tissue between the staples.
Figure 20:
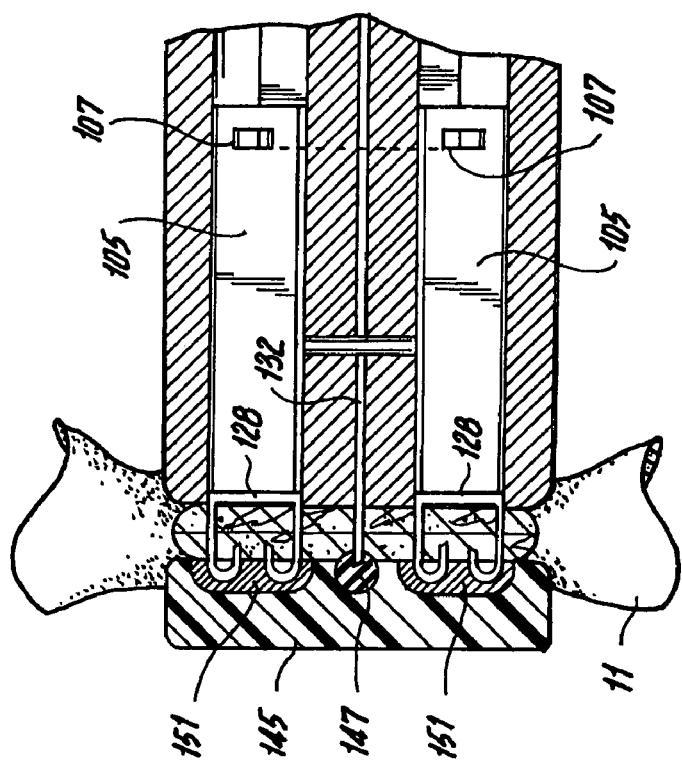
FIG. 20 is a top view of a surgical site wherein tissue has been stapled and cut by the surgical instrument of FIG. 19.

Referring to FIGS. 19 and 20, a partial cross-sectional side view and a cross-sectional top view of the staples 128 being formed and the tissue 11 being cut are shown. From the intermediate position with the tissue 11 captured, the surgeon continues to squeeze the trigger 24. The force from the trigger 24 passes through the firing linkage assembly 26 into the push-rod 83 so that the primary pusher 81, secondary pushers 105 and knife blade 132 move along arrows "d" toward the tissue 11. Near the end of travel, the secondary pushers 105 force the staples 128 into the tissue 11 and against staple forming cups 151 formed in the proximal face 146 of the anvil base 145. Substantially simultaneously, the knife blade 132 slices through the tissue 11 and comes to rest against the rod 147 of the anvil base 145. As a result, the tissue 11 is completely sheared with a staple 128 formed on each side thereof as best seen in FIG. 25. In a preferred embodiment, it only requires about 2 or 3 lbs of force to form the staples 128.

D. Retracting and Releasing

Referring now to FIGS. 21-25, various views of the fastening and cutting assembly 16 of the instrument 10 being retracted are shown. After cutting and stapling the tissue 24, the instrument 10 returns to the open position by release of the trigger 24 to reverse the sequence of motions described above. Upon release, the spring 60 pulls the rearward projection 58 downward and, thereby, the trigger 24 pivots on pin 50 and moves away from the handle portion 12. The cam pin 66 comes to rest in the bottom of the cam track 64 and this motion is translated into a rearward or proximal pull on the push-rod 83.

Figure 21:
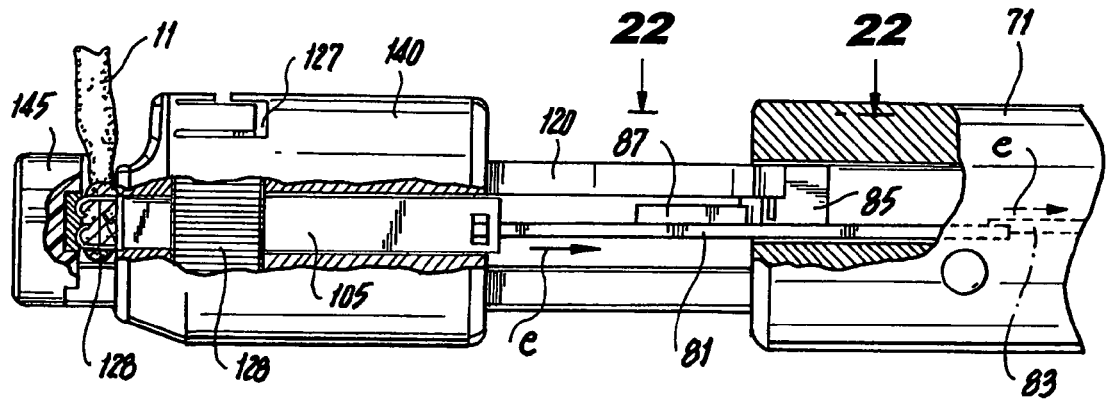
FIG. 21 is a side view, in partial cross-section, of the fastening and cutting assembly of the surgical instrument, with the primary pusher withdrawing from the anvil base and the cam follower moving such that the fastening and cutting assembly will release the stapled tissue.

Referring in particular to FIG. 21, a partial cross-sectional view of the fastening and cutting assembly 16 being retracted is shown. With a rearward pull on the push-rod 83, the primary pusher 81 moves proximally along the direction of arrow "e". As the secondary pushers 105 and knife blade 132 are coupled thereto, each of these is also retracted away from the anvil base 145.

Figure 22:
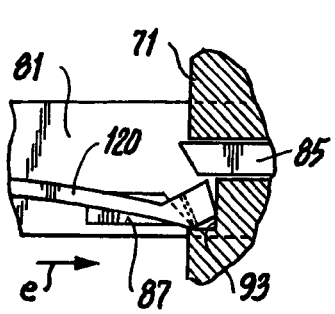
FIG. 22 is a side cross-sectional view, taken along line 22-22 of FIG. 21, showing the closer cam approaching the cam follower during withdrawal of the primary pusher from the closed, stapling position in accordance with the subject technology.
Figure 23:
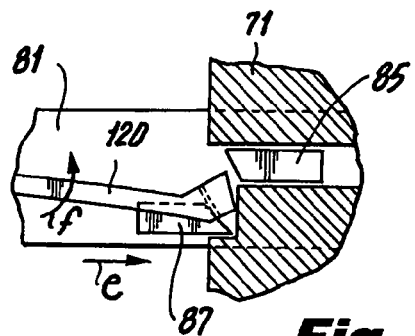
FIG. 23 is a side cross-sectional view showing the engagement of the closer cam block of the primary pusher to the cam follower to return the instrument of FIG. 22 to the open position.
Figure 24:
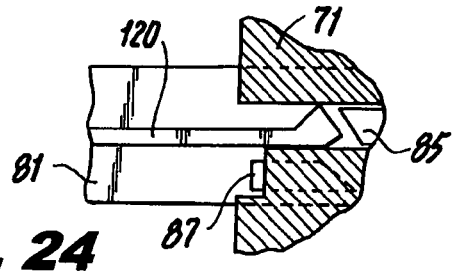
FIG. 24 is a side cross-sectional view of the surgical instrument of FIG. 22, showing the position of the cam follower in the open position after release by the release cam block.

Referring now to FIGS. 22-24, three sequential top cross-sectional views of the release cam block 87 toggling the cam follower 120 out of the intermediate position are shown. As the primary pusher 81 moves proximally along the direction of arrow "e", the release cam block 87 engages the cam follower 120 and urges the cam follower 120 out of the locked or intermediate position along the direction of arrow "f". As seen in FIG. 24, once unlocked, the cam follower 120 straightens. With the body 140 free to move, as the knife blade 132 moves proximally, the upper notch 103 engages the body 140 of the staple cartridge assembly 18 so that the body 140 moves proximally as well. The cam follower 120 again passes into the locking passage 89 until the body 140 is again in the open position and the tissue may be removed from the instrument as shown in FIG. 25. Once again open, the fastening and cutting assembly 16 is ready to continue or restart stapling and cutting to lengthen the incision while fixing the tissue 11 on each side with additional staples 128.

As can be seen, the resulting incision may cut and close a small vessel or remove a portion of tissue such as a biopsy sample. The instrument 10 may be repeatedly fired to create long incisions with adjacent staples. The incisions may be arcuate and/or linearly shaped as well as joined to form various patterns of removed tissue such as semi-circles, triangles, rectangles and the like.

VI. The Safety Lock

Referring now to FIG. 26, a proximal perspective view of staple cartridge assembly 18 ready for storage with a safety lock 180 in place is shown. Also referring to FIG. 27, an isolated perspective view of the safety lock 180 is shown. The safety lock 180 prevents accidental movement of the secondary pushers 105, knife blade 132 and body 140 relative to the anvil base 145 during storage, transportation and loading of the staple cartridge assembly 18. After loading of the staple cartridge assembly 18, the safety lock 180 is pulled upward and removed from the body 140 to activate the staple cartridge assembly 18 for use.

To accomplish the locking feature, the safety lock 180 has a depending projection 182 that rests within a notch 159 defined in the anvil arm 35. An opening 184 in the safety lock 180 surrounds the cam follower 120 when in position. A rib 186 within the opening 184 engages a notch 106 on one the secondary pushers 105. Thus, the position of the body 140 and secondary pushers 105 (and, in turn, the primary pusher 81 and knife blade 132) is set by the safety lock 180.

Several similar and alternative embodiments would be recognized by those of ordinary skill in the pertinent art based upon review of the subject disclosure. For example, without limitation, a biasing mechanism like a spring provides a distal force on the primary pusher and the trigger is configured to provide normally provide a proximal pulling force that overcomes the biasing mechanism. In order to cut and staple, the trigger is squeezed to release the proximal pulling force and allow the biasing mechanism to drive the primary pusher as noted above.

While the subject invention has been described with respect to preferred embodiments, those skilled in the art will readily appreciate that various changes and/or modifications can be made to thereto without departing from the spirit or scope of the invention as defined by the appended claims.

What is claimed is:

1. An instrument for stapling and cutting body tissue comprising:
   a) a handle portion for actuating and controlling placement of the instrument;
   b) a pusher housing having a proximal end coupled to the handle portion, the pusher housing defining a pusher axial passage having a hollow;
   c) a primary pusher slidably received in the pusher axial passage, the primary pusher having a cam surface;
   d) an anvil assembly having an arm coupling to the pusher housing and a base located on a distal end of the aim;
   e) a cartridge body slidably mounted on the arm, the body including a distal face and a proximal face, the body defining an axial bore and at least one staple passage;
   f) a cam follower extending from the proximal face;
   g) a release cam block upstanding from the primary pusher;
   h) a knife blade coupled to the primary pusher for sliding movement in the axial bore; and
   i) at least one staple in the at least one axial staple passage, wherein in an open position, the handle portion is used to place tissue in between the anvil base and the distal face of the cartridge body, in an intermediate position, the handle portion has actuated the primary pusher such that the cam surface has moved the cam follower into a locked position in the hollow and, thereby, the tissue is clamped, and in a fastened and cut position, the handle portion has further actuated the primary pusher such that the staple has been driven and formed in the tissue and the knife blade has cut the tissue against the anvil base, and wherein as the primary pusher returns to the open position, the release cam block dislodges the cam follower from the hollow to allow the cartridge body to move.

2. An instrument for stapling and cutting body tissue comprising:
   a) a handle portion for actuating and controlling placement of the instrument;
   b) a pusher housing having a proximal end coupled to the handle portion, the pusher housing defining a pusher axial passage having a hollow;
   c) a primary pusher slidably received in the pusher axial passage, the primary pusher having a cam surface;
   d) an anvil assembly having an arm coupling to the pusher housing and a base located on a distal end of the arm;
   e) a cartridge body slidably mounted on the arm, the body including a distal face and a proximal face, the body defining an axial bore and at least one staple passage;
   f) a cam follower extending from the proximal face;
   g) a safety lock for preventing accidental movement;
   h) a knife blade coupled to the primary pusher for sliding movement in the axial bore; and
   i) at least one staple in the at least one axial staple passage, wherein in an open position, the handle portion is used to place tissue in between the anvil base and the distal face of the cartridge body, in an intermediate position, the handle portion has actuated the primary pusher such that the cam surface has moved the cam follower into a locked position in the hollow and, thereby, the tissue is clamped, and in a fastened and cut position, the handle portion has further actuated the primary pusher such that the staple has been driven and formed in the tissue and the knife blade has cut the tissue against the anvil base, and wherein the safety lock has a depending projection that rests within a notch defined in the arm and defines an opening sized to receive the cam follower.

3. An instrument as recited in claim 2, wherein the safety lock has a rib within the opening for engaging the primary pusher.

4. An instrument for stapling and cutting body tissue comprising:
   a) a handle portion for actuating and controlling placement of the instrument;
   b) an elongated pusher housing having a proximal end coupled to the handle portion, the pusher housing defining a locking passage and a pusher axial passage having a hollow;
   c) a primary pusher slidably received in the pusher axial passage, the primary pusher being a plate with a closer cam block and a release cam block upstanding therefrom; and
   d) a cartridge assembly coupled to the pusher housing, the cartridge assembly including:
      i) a body with a distal face and a proximal face and a cam follower extending from the proximal face, the body defining an axial bore, two opposing axial staple passages and opposing staple load passages;
      ii) an anvil assembly having an arm extending through the axial bore and coupled to the locking passage, the anvil assembly having a base located on a distal end of the arm wherein a proximal face of the base forms a tissue gap with the distal face of the body;
      iii) a knife blade coupled to the primary pusher for sliding movement in the axial bore;
      iv) a first secondary pusher coupled to the primary pusher for sliding movement in one of the axial staple passages;
      v) a second secondary pusher coupled to the primary pusher for sliding movement in the other of the axial staple passages; and
      vi) staples in the axial staple passages,
      wherein in a normally open position, the handle portion is used to place tissue in the tissue gap,
      in an intermediate position, the handle portion has actuated the primary pusher such that the closer cam block has moved the cam follower such that the cam follower is locked in the hollow to clamp the tissue,
      in a fastened and cut position, the handle portion has further actuated the primary pusher such that the first and secondary pushers have each driven and formed a staple in the tissue and the knife blade has cut the tissue, and
      wherein as the primary pusher returns to the open position, the release cam block dislodges the cam follower from the hollow to allow the body to move.

5. An instrument for stapling and cuffing body tissue comprising:
   a) a handle portion for actuating and controlling placement of the instrument;
   b) an elongated pusher housing having a proximal end coupled to the handle portion, the pusher housing defining a locking passage and a pusher axial passage having a hollow;

c) a primary pusher slidably received in the pusher axial passage, the primary pusher being a plate with a closer cam block and a release cam block upstanding therefrom; and d) a cartridge assembly coupled to the pusher housing, the cartridge assembly including:

i) a body with a distal face and a proximal face and a cam follower extending from the proximal face, the body defining an axial bore, two opposing axial staple passages and opposing staple load passages;

ii) an anvil assembly having an arm extending through the axial bore and coupled to the locking passage, the anvil assembly having a base located on a distal end of the aim wherein a proximal face of the base forms a tissue gap with the distal face of the body;

iii) a knife blade coupled to the primary pusher for sliding movement in the axial bore;

iv) a first secondary pusher coupled to the primary pusher for sliding movement in one of the axial staple passages;

v) a second secondary pusher coupled to the primary pusher for sliding movement in the other of the axial staple passages; and vi) staples in the axial staple passages, wherein in a normally open position, the handle portion is used to place tissue in the tissue gap, in an intermediate position, the handle portion has actuated the primary pusher such that the closer cam block has moved the cam follower such that the cam follower is locked in the hollow to clamp the tissue, in a fastened and cut position, the handle portion has further actuated the primary pusher such that the first and secondary pushers have each driven and formed a staple in the tissue and the knife blade has cut the tissue, and wherein the pusher housing further defines a first transaxial bore for receiving an anvil pin to lock the anvil assembly therein.

6. An instrument for stapling and cuffing body tissue comprising:

a) a handle portion for actuating and controlling placement of the instrument;

b) an elongated pusher housing having a proximal end coupled to the handle portion, the pusher housing defining a locking passage and a pusher axial passage having a hollow;

c) a primary pusher slidably received in the pusher axial passage, the primary pusher being a plate with a closer cam block and a release cam block upstanding therefrom;

d) a safety lock for preventing accidental movement; and e) a cartridge assembly coupled to the pusher housing, the cartridge assembly including:

i) a body with a distal face and a proximal face and a cam follower extending from the proximal face, the body defining an axial bore, two opposing axial staple passages and opposing staple load passages;

ii) an anvil assembly having an arm extending through the axial bore and coupled to the locking passage, the anvil assembly having a base located on a distal end of the arm wherein a proximal face of the base forms a tissue gap with the distal face of the body;

iii) a knife blade coupled to the primary pusher for sliding movement in the axial bore;

iv) a first secondary pusher coupled to the primary pusher for sliding movement in one of the axial staple passages;

v) a second secondary pusher coupled to the primary pusher for sliding movement in the other of the axial staple passages; and vi) staples in the axial staple passages, wherein in a normally open position, the handle portion is used to place tissue in the tissue gap, in an intermediate position, the handle portion has actuated the primary pusher such that the closer cam block has moved the cam follower such that the cam follower is locked in the hollow to clamp the tissue, and in a fastened and cut position, the handle portion has further actuated the primary pusher such that the first and secondary pushers have each driven and formed a staple in the tissue and the knife blade has cut the tissue, and wherein the safety lock has a depending projection that rests within a notch defined in the arm and defines an opening sized to receive the cam follower.

7. A fastening and cutting assembly for stapling and cutting body tissue comprising:

a) a housing defining an axial passage;

b) a pusher slidably received in the axial passage, the pusher having a cam surface;

c) an arm coupled to the housing;

d) an anvil base located on the arm;

e) a cartridge body slidably mounted on the arm between the housing and the base, the cartridge body defining an axial bore and at least one staple passage;

f) a cam follower extending from the cartridge body to the housing;

g) a knife blade coupled to the pusher for sliding movement in the axial bore;

h) at least one staple in the at least one axial staple passage, wherein in an open position, tissue can be placed between the anvil base and the cartridge body, and in an intermediate position, the cam surface of the pusher can move the cam follower into a locked position and, thereby, the tissue can be clamped between the cartridge body and the anvil base; and i) a safety lock for preventing accidental movement, wherein the safety lock has a depending projection that rests within a notch defined in the arm and defines an opening sized to receive the cam follower.

* * * * *